United States Patent [19]
Alt et al.

[11] Patent Number: 5,649,968
[45] Date of Patent: Jul. 22, 1997

[54] ACCELEROMETER-BASED RATE-ADAPTIVE CARDIAC PACING WITH SECOND GENERATION SIGNAL PROCESSING

[75] Inventors: Eckhard Alt, Ottobrunn, Germany; Lawrence J. Stotts, Lake Jackson, Tex.; Matthias Schmidt, Munich, Germany

[73] Assignee: Intermedics, Inc., Angleton, Tex.

[21] Appl. No.: 557,204

[22] Filed: Nov. 14, 1995

[51] Int. Cl.$^6$ .................................................. A61N 1/362
[52] U.S. Cl. .................................................. 607/19
[58] Field of Search .................. 607/4, 9, 17–19, 607/14, 25

[56] References Cited

U.S. PATENT DOCUMENTS

| | | | |
|---|---|---|---|
| 5,016,632 | 5/1991 | Hoegnelid et al. | 607/19 |
| 5,031,615 | 7/1991 | Alt | 607/19 |
| 5,040,535 | 8/1991 | Mann et al. | 607/19 |
| 5,179,947 | 1/1993 | Meyerson et al. | 607/19 |
| 5,330,510 | 7/1994 | Legzy et al. | 607/19 |
| 5,360,436 | 11/1994 | Alt et al. | 607/18 |
| 5,383,911 | 1/1995 | Mann | 607/19 |

*Primary Examiner*—William E. Kamm
*Assistant Examiner*—George R. Evanisku
*Attorney, Agent, or Firm*—Wigman, Cohen, Leitner & Myers, P.C.

[57] ABSTRACT

A variable rate cardiac pacemaker is adapted to be implanted in a human patient for automatically adapting pacing rate to metabolic need of the patient when the patient is walking in an ascending path, a descending path, or on a level plane. An accelerometer senses the activity of the patient walking, and produces an electrical sensor signal representative of the activity. The accelerometer signal has variable parameters indicative of morphology, including amplitude, of the sensor signal according to status of activity of the patient and to the upward, downward, or horizontal direction of the patient's walking. A pulse generator generates pacing pulses at a variable rate according to an applied control signal to electrically stimulate the patient's heart at a pacing rate which varies according to patient activity. A processing and control circuit of the pacemaker processes the sensor signal for detecting differences in the signal morphology attributable to whether the patient is walking on an ascending path, a descending path, or a level path, irrespective of the presence or absence of disparity in the amplitude of the sensor signal resulting from walking along the respective path. The latter circuit also develops the control signal to dictate a basic pacing rate from the amplitude of the sensor signal, and an enhanced rate more appropriate to the metabolic need of the patient from the detected differences in morphology of the sensor signal, for application to the pulse generator.

17 Claims, 3 Drawing Sheets

ACCELEROMETER-BASED RATE-ADAPTIVE CARDIAC PACING WITH SECOND GENERATION SIGNAL PROCESSING

BACKGROUND OF THE INVENTION

The present invention relates generally to implantable cardiac pacemakers responsive or adaptive to patient exercise, as detected by movement or activity of the patient, to generate an appropriate pacing rate. More particularly, the invention pertains to a rate-adaptive pacemaker which develops an appropriate rate response to a specific type of exercise by the patient based on morphology of the signal generated by the activity sensor.

Since its introduction into clinical practice, rate-adaptive pacing has gained widespread application. Currently, more than 50% of all pacemakers implanted worldwide employ means for varying pacing rate based on data provided by one or more sensors.

The aim of rate-adaptive pacemakers is to pace the heart with a variable rate that matches the metabolic needs of the body, according to the state of rest or exercise of the patient. An adequate rate adaptation is mandatory to permit full physical capability of the patient. German Patent No. DE 34 19 439 and related U.S. Pat. No. 4,688,573 disclose a rate-adaptive pacer responsive to central venous blood temperature, with algorithms defining heart rate as a function of the latter for states of rest and exercise, and a decision rule for selection of an appropriate algorithm in a given situation. Various other physiologic parameters that have been proposed for detection and use in rate-adaptive pacing include blood oxygen saturation, respiration, and chest impedance (minute ventilation). These intrinsic parameters respond relatively slowly to changes in level of patient exercise, with concomitant delay in change in pacing rate. Moreover, the parameter sensors are expensive precision devices typically requiring complex surgical implant procedures.

To achieve a more physiologic, rapid response of pacing rate to patient activity with a low cost sensor and relatively uncomplicated implant procedure, the technology has moved to the use of pure activity sensors designed to detect movement or exercise of the patient directly, rather than the indirect sensing that had been principally employed. Detection of the patient's physical activity is now the most widespread principle used for rate-adaptive pacing.

The first rate-adaptive pacemaker employing activity sensing may have been disclosed in U.S. Pat. No. 4,140,132 to Dahl. A mechanoelectrical converter consisting of a weighted cantilever arm and piezoelectric crystal in the implanted pacer underwent mechanical vibrations in reponse to patient movement. These vibrations were converted by the crystal to an electrical output signal, which was used to control the variable rate pulse generator of the pacemaker. U.S. Pat. No. 4,428,378 to Anderson is to similar effect, the amplitude of the high frequency content of the converter output signal being a bandpass signal to control pacing rate.

Activity or motion sensors provide virtually immediate response to patient movement for pacing rate control, but have disadvantages of sensitivity to noise and other disturbances which contribute improperly to the pacing rate. The Anderson '378 patent proposes that the maximum sensitivity of the device be in a frequency range above 10 Hertz (Hz), which it assumed to be the resonant frequency range of the major body compartments such as thorax and abdomen, and thought to be where the maximum value of pedal impact detected by the sensor would occur.

In contrast, U.S. Pat. No. 4,926,863 to Alt teaches that the activity sensor output signal indicative of true physical exercise actually occurs in a frequency range well below 10 Hz—at about 4 Hz or less—and that this range is virtually devoid of frequencies of disturbances unrelated to exercise. This low frequency band and different baseline values established for comparison have been shown to enable rapid, accurate rate response, especially where the activity sensor is an accelerometer. The accelerometer may also be conveniently located within the pulse generator housing, with resulting cost benefit and ease of implantation.

Other improvements in rate-adaptive pacers using an accelerometer as the activity sensor are disclosed in U.S. Pat. No. 5,031,615 to Alt, which describes manufacture of the accelerometer with related processing circuitry integrated in hybrid semiconductor circuitry as a microminiature, low power mechanoelectrical transducer that filters the signal to pass only components in the band below about 4 Hz. U.S. Pat. No. 5,014,703 to Alt discloses an activity pacemaker that discriminates between patient movements attributable to true physical exercise and detected indicia arising from other causes (e.g., riding on a rough road surface) samples the output signal over successive time intervals to assess the trend of patient exercise, and to adjust pacing rate accordingly. U.S. Pat. No. 5,031,614 to Alt uses frequency and amplitude of accelerometer signal to control pacing rate, both of those components obtained from signal amplitude only, using a moving window technique. Co-pending application Ser. No. 08/279,946 to Alt discloses use of a distinct nonlinearity of the accelerometer signal to discriminate between types of patient exercise, such as walking and bicycling, despite same or similar workload, and to adjust pacing rate.

Accelerometer-based pacemakers have provided the most physiologically adequate rate adaptation with fast response time and gradually increasing pacing rate with increasing physical activity. This is especially true for walking—the most popular form of exercise for pacemaker patients. Several clinical studies have demonstrated the linear correlation between pacing rate and workload when the patient's walking speed is gradually increased.

A recent article titled "Intrinsic heart rate response as a predictor of rate-adaptive pacing benefit", E. Alt et al., *Chest* 1995, 107:925–30, describes the strong correlation between the body's oxygen uptake and accelerometer controlled pacing rate with walking.

Accelerometer-based pacing devices have successfully overcome many of the limitations of previous activity pacemakers, such as when patients walk on different grades, including horizontal surfaces, up and down stairs at a regular walking speed of 72 steps per minute. A recent study conducted by the applicants herein supports this finding, as reported in "Activity-controlled cardiac pacemakers during stair-walking; a comparison of accelerometer to vibration-guided devices and to sinus rate", E. Alt et al., *PACE* 1995). But this study also found that with higher walking speeds, such as 84, 92, 96, 108, or 120 steps per minute, which represents relatively fast walking, differences in pacing rate between walking on level surface, up stairs, and down stairs disappear. That is, under those conditions the accelerometer-based devices provide virtually the same pacing rate independent of the type of activity the patient is engaging in at the higher walking rates.

This behavior departs significantly from the normal rate behavior, in which, for example, walking upstairs yields the highest sinus rate, and walking downstairs yields the lowest sinus rate compared with the medium rate of walking on a horizontal surface, assuming the same walking speed for all three types of activity.

It is a principal aim of the present invention to provide methods and means to improve the performance of rate-adaptive pacemakers based on more accurate detection of physical activities with an accelerometer, toward more physiologic regulation.

A related object of the invention is to provide techniques for detecting and distinguishing types of patient physical exercise from one another, using the morphology of the activity signal, so as to enhance the pacing of the patient's heart at rates most closely approximating the true physiologic rate for the type of exercise involved.

SUMMARY OF THE INVENTION

Heretofore, the pacing rate has been based primarily on the amplitude of the activity sensor signal. Variations of the amplitude of the activity sensor signal are indicative of changes in level or intensity of exercise, and are used in activity pacemakers to vary the pacing rate accordingly. However, it has been found that in some forms of physical exercise, the amplitude of the activity sensor signal is substantially the same despite differences in the type of activity involved, which are manifested by differences between the heart rates of healthy individuals with normal cardiovascular systems engaged in such different forms or types of activity.

For example, in tests conducted by the applicants on one control group numbering sixteen pacemaker patients of nine males and seven females, having a mean age of 64.4 years, each patient was fitted with an accelerometer-based activity (rate-adaptive) pacemaker (manufactured by Intermedics, Inc. of Angleton, Tex.) affixed to the chest. The patients walked on level surface (i.e., horizontal, with no grade), walked up steps of a stairway, and walking down steps of a stairway, at five different step rates set by an acoustic quartz metronome. The accelerometer signal was recorded on a portable TEAC R71 data recorder, and run through a simulated leaky integrator using Lab View software (of National Instruments Corp., Austin, Tex.) for analysis with respect to the peak average of the mean acceleration. The accelerometer signal is representative of anterior-posterior movement of the patient, not the up-down movement. Hence, the signal does not depend on the intensity at which the patient's feet are hitting the ground during walking, or on different gaits of walking. Ultimately, the analysis concentrated on characteristics of the raw acceleration signal above and below a baseline of electrical zero.

It was observed that approximately the same accelerometer signal amplitude was obtained when the patients walked on a level surface, up stairs, or down stairs, for each of the different step rates of 72, 84, 96, 108, and 120 steps per minute, in consecutive time intervals. The five successive changes in step rate displayed a linear increase in amplitude for increase in the step rate. But the signal pattern or form (i.e., its morphology) remained approximately the same throughout for each type of activity, despite increases in step rate. The pattern was exemplifed by a zero baseline with quite similar peaks above and below the baseline according to the frequency of the walking. The activity signal morphology differed, however, for the three different types of activity, despite the fact that the patients were paced (by the metronome) to walk at about the same rate for each grade, e.g., 72 steps per minute whether walking on a level surface, an ascent, or a descent.

The term "grade," when used in this specification, is intended to mean and include a reference level (e.g., a horizontal or "level" surface or path), as well as a change in elevation (e.g., such as of a stairway or a sloping path that requires ascent or descent), all of which are within the standard dictionary definition of that term. Thus, the terminology "different grades" encompasses a level path (a substantially expansive horizontal surface), an ascending path (an "up" staircase, as well as an "up" slope), and a descending path (a "down" staircase, as well as a "down" slope).

In the aforementioned tests, the pacemaker pulse generator was affixed in each patient in the pectoral region. In some patients, the generator was placed on the left side with the manufacturer's logo facing outward, which is the normal orientation of the device, while in other patients, it was placed on the right side with the logo facing down. This was done simply to allow the cables to be directed to the proper side for signal recording, and is mentioned here only because it produced an inversion of the signal morphology between the two orientations, but all other characteristics of the accelerometer signal were substantially duplicated in both sets of patients in the group.

When the patients walked up stairs, the sharper movement in the recorded signal pattern representing the morphology of the accelerometer signal was in the downward direction (i.e., below the zero baseline); while in the case of walking down stairs, the sharper movement in the recorded signal pattern was almost exactly the opposite, with the larger signal excursions above the baseline. This was found to be consistent across many different patients in different control groups. Thus, different signal patterns are encountered for patients walking upstairs, walking on a level surface, and walking downstairs.

It then becomes necessary to determine how these differences in signal morphology may be most easily and simply detected, so that the pacing rate can be controlled to be properly responsive to the particular activity. According to a preferred embodiment of the invention, the amplitude of the activity signal is analyzed to establish the base pacing rate of the implanted device, and the signal morphology is then used to enhance or "trim" or "tune" the rate to make it more appropriate ("more adequate") to the patient's specific activity.

As pointed out in the Background section above, the principle of acceleration controlled, rate adaptive pacing has been described in previous patents. The same is true for various types of processing of the accelerometer signal, including, for example, delta modulation, detection of peak average, peak threshold, zero crossing, amplitude, integration, and so forth. U.S. Pat. No. 5,360,436 to Alt discloses a device that is capable of distinguishing between different types of patient movement, using somewhat complex pattern recognition techniques, and of comparing the instantaneously detected accelerometer signal with a template matching the type of activity engaged in by the patient to provide an appropriate pacing rate. Such signal processing is both elegant and specific, but it requires considerable memory and logic processing capability within the implanted pacemaker (or device designed to provide appropriate response to other dysrhythmias as well, such as tachycardia and fibrillation, in a combined pacer, cardioverter, and defibrillator). The energy requirements are such that battery drain is higher than that occurring with standard signal processing means.

So with respect to the present invention, the desire is not only to analyze the morphology of the activity signal from which to discern the specific type of activity—as between walking on the horizontal, walking on an ascent, and walking on a descent—and to control the pacing rate of the implanted device accordingly, but to do so in a manner that does not result in an untoward energy penalty. One way to achieve this end is to look at the signal amplitude and compare its peaks above and below the baseline value (typically, the electrical zero level). Another way to do this is to look at zero crossings with an appropriate threshold to examine how much of the signal is above and how much is below the baseline, akin to a probability density function. Yet another technique is to look at how long the signal pattern spends above and how long below the baseline. Many other techniques of taking advantage of the principles of the present invention are also available.

In the preferred embodiment, the accelerometer signal content above and below the baseline are calculated, and a ratio of the two is obtained by computing their quotient—as ratio of the amplitudes above and below, or time span above and below, or areas between zero crossings above and below the baseline—a fixed or even a floating (corrected) baseline. It may be necessary that, rather than the electrical fixed zero, a low pass filtering at 0.1 Hz or the like is used to provide a moving baseline, in the observation of signal content (peak, area, time, baseline crossings, etc.) above and below the baseline.

On average, for human subjects walking at 108 steps per minute, the heart rate without artificial cardiac pacing should be 102 beats per minute (bpm) when walking on a level surface, 132 bpm when walking up stairs, and 107 bpm when walking down stairs. With the usual first generation algorithm, which, again, is based primarily on the activity signal amplitude, the paced heart rate for the control group patients was 128 bpm, 130 bpm, and 117 bpm, respectively, for these three different grades. Clearly, these paced rates were not completely faithful representations of the normal, unpaced heart rates.

According to the invention, a second generation signal processing algorithm of the types mentioned above is utilized to reflect the pattern or morphology, as well as the amplitude, of the accelerometer signal, so as to control the artificial cardiac pacing rate delivered by an implanted pacemaker in a manner that more accurately duplicates the normal heart rate under the same conditions of exercise/ activity. The algorithm provides a first determinant or generation of activity signal amplitude, and a second determinant or generation of activity signal pattern to enhance the rate control. In an exemplary embodiment, the proportions of the signal lying above and below the baseline were determined, and their ratio calculated. If the ratio exceeds unity (i.e., a greater proportion of the signal is above the baseline), it is indicative that the patient is walking down stairs, calling for a modification of the rate from the above 117 bpm first generation rate to, say, 103 bpm. On the other hand, if the ratio is less than unity (i.e., a greater proportion of the signal is below the baseline), it is indicative that the patient is walking up stairs, calling for a modification of the rate from the above 130 bpm to, say, 124 bpm. For walking on a level surface, approximately the same proportions of the signal lie above and below the baseline, so that the ratio is at or near unity. In the latter case, the pacing rate is tuned from the 128 bpm rate to 114 bpm. Thus, despite the accelerometer signal having the same amplitude whether the subject is moving along a level surface or up or down stairs, a pacing rate is selected that better matches the patient's current metabolic need.

The same holds true regardless of the walking speed of the patient. Accordingly, not only is the signal amplitude processed, but the morphology of the accelerometer signal is considered—either the absolute morphology as a template, or in relation to an electrical baseline, or in relation to a floating, low pass average baseline. An even better indication of type of activity is obtained by squaring the positive and negative signal content before taking the ratio.

Observation of the activity signal morphology to enhance the control of pacing rate can be achieved, for example, by filtering with different filter settings, or by integrating the area, or by pattern templates, or by peak differentiation of the acceleration maximum over dt, or by extracting the highest frequency component. In one embodiment, the means for evaluating the signal morphology include the activity sensor itself, an amplifier followed by a rectifier for processing the sensor signal, a leaky integrator, and two rectifiers, one for the positive portions of the sensor signal, and the other for the negative portions, relative to the electrical zero—so that both portions may be evaluated. The effect is that of using two leaky integrators, which provide information on positive and negative signal content, relative to electrical zero.

Alternatively, a filter may be used with a time constant of 10 seconds, so that after 10 seconds the device returns to the baseline. Instead, zero crossings over electrical zero may be determined while establishing a threshold. This enables a small threshold for zero crossings to observe the amounts of positive and negative zero crossings occur within a predetermined period of time. Then positive and negative portions may be compared, as well as a comparison of length, or of area of the signal vis-a-vis zero crossings. The raw signal is run through a low pass filter for purposes of signal averaging.

Ultimately, an important object of the invention is to use a non-metabolic sensor, and nevertheless to provide as faithful a metabolic response as possible, which mimics the normal heart rate for the activity. Therefore, despite use of a relatively "primitive" activity-type sensor which only provides signals based on mechanical movement, the response is improved to provide an adequate metabolic response as well by extracting more from those purely mechanical signals than mere amplitude.

Accordingly, in one of its aspects, the invention provides a variable rate cardiac pacemaker adapted to be implanted in a human patient, for automatically adapting pacing rate to metabolic need of the patient when walking upwardly, downwardly, or on the horizontal, in which a sensor is responsive to patient walking to produce an electrical sensor signal representative of activity of the patient's body during such walking, the sensor signal having variable parameters indicative of morphology including amplitude of the sensor signal according to status of activity of the patient and to whether the walking of the patient is upward, downward or on a horizontal surface; a pulse generator generates pacing pulses at a variable rate according to an applied control signal to electrically stimulate the patient's heart at a pacing rate which varies according to patient activity; and control means are adapted to process the sensor signal for detecting differences in signal morphology attributable to whether the patient is walking upwardly, downwardly, or horizontally, irrespective of presence or absence of distinctions in amplitude of the sensor signal therefrom, and for developing the control signal to dictate a basic pacing rate from the amplitude of the sensor signal and an enhanced rate more appropriate to the metabolic need of the patient from the detected differences in morphology of the sensor signal, for application to the pulse generator.

In another aspect, the invention provides a method of artificial cardiac pacing in a human patient using an implanted pacemaker device to automatically vary pacing rate according to patient activity, including sensing patient activity and producing an electrical sensor signal indicative thereof having a signal morphology that varies in at least some signal characteristics according to whether the patient activity involves walking upstairs, downstairs, or on a horizontal surface; controllably generating pacing pulses at a variable rate adapted to electrically stimulate the patient's heart at a rate that reflects metabolic need arising from patent activity; and responding to the sensor signal and to variations in at least some characteristics of the signal morphology attributable to the patient walking upstairs, downstairs, or on a horizontal surface, and controlling the pacing rate according to the morphology characteristics variations.

BRIEF DESCRIPTION OF THE DRAWINGS

The above and other objects, aspects, features and attendant advantages of the present invention will become apparent from a consideration of the ensuing detailed description of presently contemplated best mode of practicing the invention, by reference to certain preferred embodiments and methods, taken in conjunction with the accompanying drawings, in which.

DETAILED DESCRIPTION OF THE PREFERRED EMBODIMENT AND METHOD

An analysis of the characteristics of a patient's physical movement associated with different types of physical activity may be achieved using a large database of recorded accelerometer signals. In another study conducted with forty-five subjects of different age and exercise capabilities, the unfiltered signal of an accelerometer in a pacemaker pulse generator worn by each subject was detected and amplified, for three individual activities, viz., walking on a level surface (i.e., on the horizontal), walking up stairs (i.e., up a grade or ascending), and walking down stairs (i.e., down a grade or descending). Each activity was conducted at step rates 72, 84, 96, 108, and 120 steps per minute.

Figure 1A:
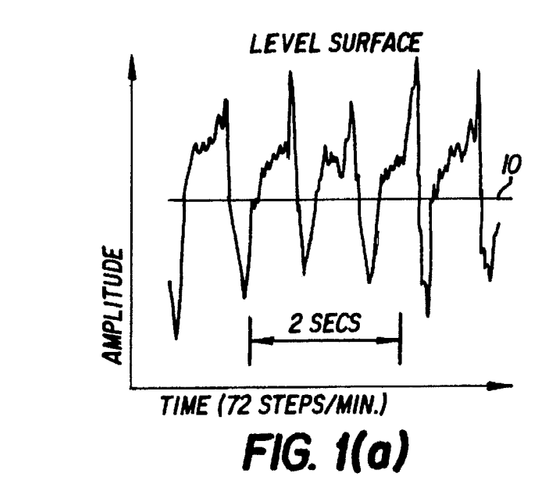
FIGS. 1(a), (b), and (c) are strip charts representative of the accelerometer signal amplitude variations over a selected interval of patient activity consisting of walking on a level surface, up a set of stairs, and down a set of stairs, respectively, at a particular walk rate.
Figure 1B:
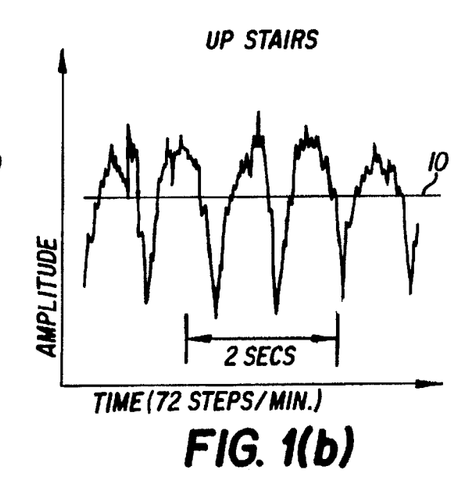
Figure 1C:
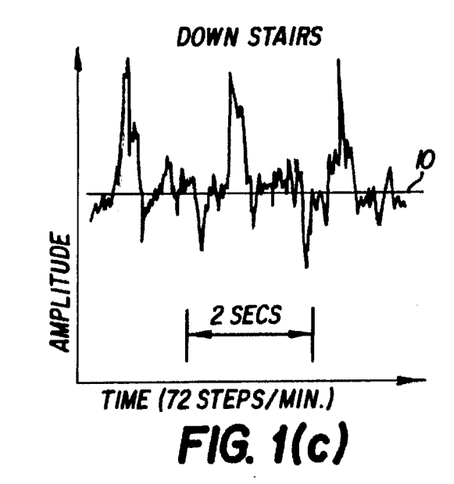

The morphology of the accelerometer signals for the three types of walking activity by a subject which was generally representative of the results obtained for all subjects in the study, is illustrated in parts (a), (b), and (c) of FIG. 1. The acceleration level was detected using the Lab View software as a simulated leaky integrator. Each of the three strip charts is representative of the accelerometer signal amplitude variations over a total of about six seconds, with emphasis for present purposes of this explanation on the centrally located two second interval of the respective chart, for walking on a level surface (FIG. 1(a)), up stairs (FIG. 1(b)), and down stairs (FIG. 1(c)), in each instance at 72 steps per minute paced by an acoustic quartz metronome. Of course, much longer periods of such activity were obtained and analyzed for each subject, but the results indicated by these isolated strip portions are typical for each case.

The charts indicate somewhat similar accelerometer signal patterns for the level surface and down stairs walking activity, with sharper or spiky portions both upward and downward (but particularly for the amplitude of the positive peaks) from the baseline 10. In contrast, the signal amplitude variations obtained from walking up a set of stairs, FIG. 1(b), show a more measured or deliberate movement of the patient, indicative of greater exertion. It will also be observed that some similarities also exist in the signal characteristics of the charts of FIGS. 1(a) and 1(b), such as between zero crossings.

Figure 2:
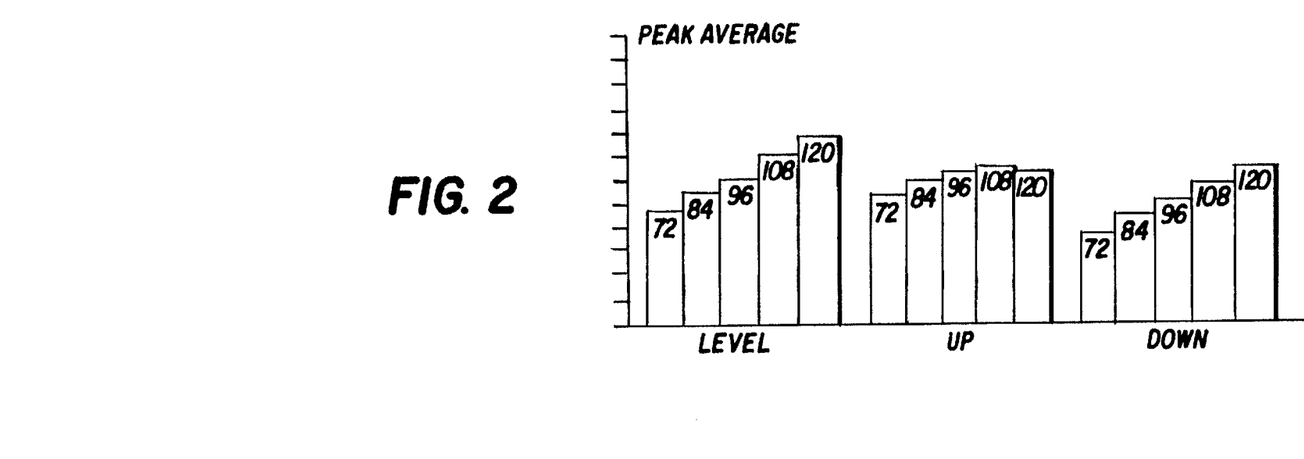
FIG. 2 is a bar chart of peak average amplitude of accelerometer signal for level, up, and down grades, respectively, at walking speeds from 72 to 120 steps/minute.

FIG. 2 contains three bar charts, illustrating results obtained from leaky integrator processing of the amplitudes of the accelerometer signals for walking step rates of 72, 84, 96, 108, and 120 steps per minute on a horizontal, up stairs, and down stairs, respectively. It will be observed that the acceleration level for walking down stairs, especially at the higher step rates, would yield an inappropriately high pacing rate if the leaky integrator signal were used as a direct rate control signal.

Figure 3:
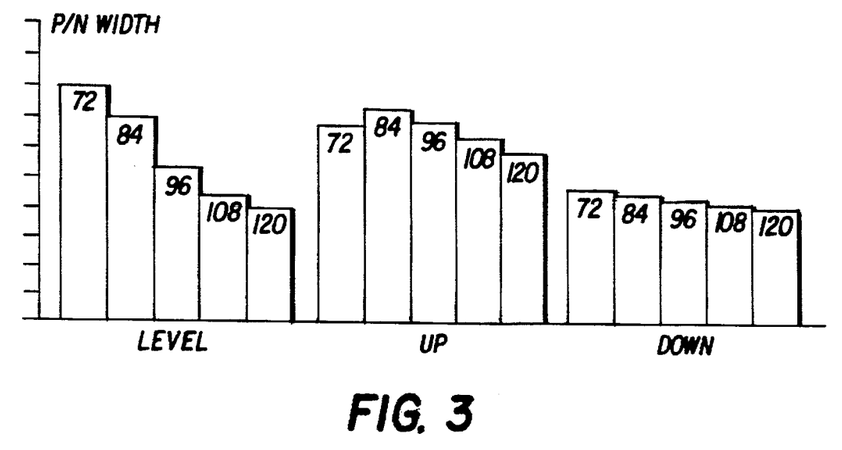
FIG. 3 is a bar chart of the quotient of the width of the positive (P) portion divided by the width of the negative (N) portion of the accelerometer signal for level, up, and down grades, respectively, at walking speeds from 72 to 120 steps/minute.

Therefore, in one embodiment of the invention, the characteristics of the accelerometer signal above and below a baseline representing zero acceleration are analyzed by comparing the durations of the signal in positive and negative directions above and below the baseline, respectively. Signal processing is performed by calculating the quotient of the length or area represented by consecutive zero crossings for positive divided by negative values, which by reference to FIG. 3, can be seen to yield significant information from which to discriminate between the three types of activity.

Figure 4:
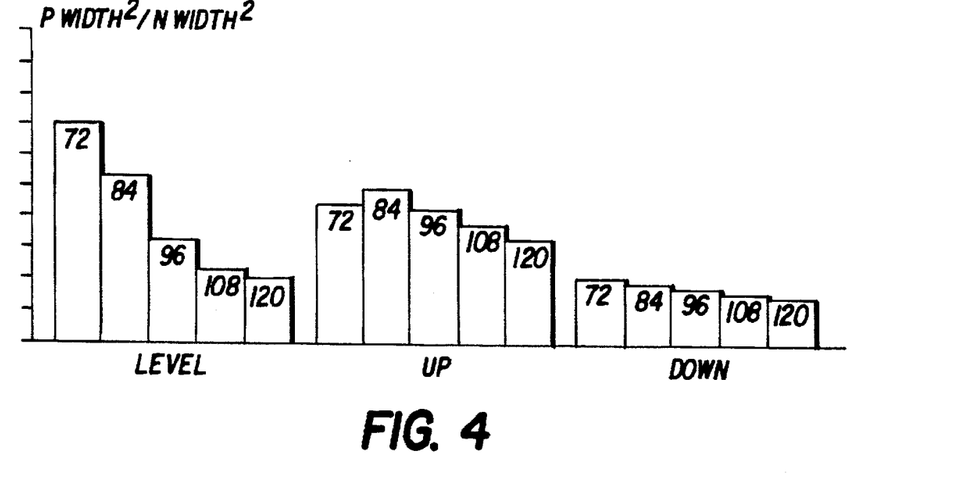
FIG. 4 is a bar chart for P/N width squared of accelerometer signal for level, up, and down grades, respectively.

The combination of the amplitude and area of the acceleration signal indirectly detected by the leaky integrator with the time characteristics of the signal above and below the baseline, as detected by zero crossings, can serve as a rate control signal to yield a more appropriate pacing rate response to the three different types of patient walking activity addressed here. The differentiation between walking up and down stairs is even more pronounced if the duration of the accelerometer signal above and below the zero baseline are each squared before dividing the two to obtain the quotient (ratio thereof), as illustrated by FIG. 4.

In simulation studies performed by the applicants herein, it was demonstrated that for each patient, a certain weighting factor for the quotient of the positive and negative time domain assists in providing a more specific rate response to accentuate the distinction between walking downstairs and walking upstairs or on a relatively level surface. In particular, the rate response to walking down stairs is attributable to a considerably lower quotient than that obtained when the patient is walking on a level surface or up stairs. This result is shown in FIG. 5.

The distinction is especially pronounced if the maximum positive signal is limited to a specific value such as 1.5, relative to the maximum lower level limited to a factor of 1.0. Then the signal content derived from the accelerometer provides specific information that allows adjustment of the pacing rate to more directly meet the metabolic needs of the patient for the particular type of walking activity. That is, the highest pacing rate is achieved with walking up stairs, and the lowest pacing rate is achieved with walking down stairs, regardless of the actual walking speed of the patient.

Figure 5:
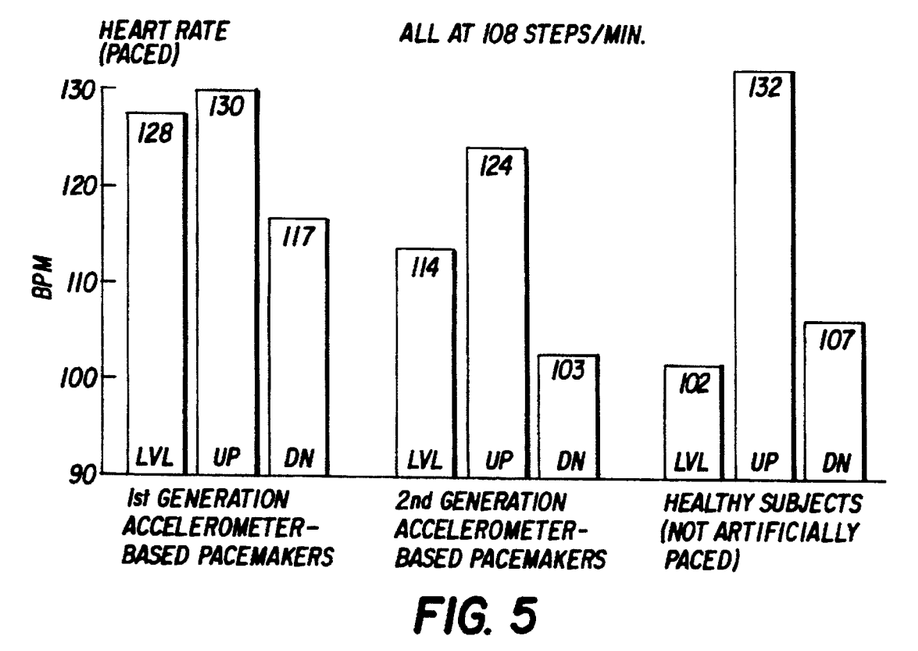
FIG. 5 is a bar chart showing heart rate with first generation pacing, with second generation pacing, and for healthy subjects, respectively, for a walk rate of 108 steps per minute, and for level, up, and down grades, respectively.

With reference to FIG. 5, it will be observed that the pacing rates for the second generation signal processing (indeed, examining and using virtually any of the accelerometer signal morphology characteristics beyond mere amplitude of the signal) yield a much more representative counterpart with second generation (middle portion of chart) relative to normal healthy heart rate (fight portion of chart), than with first generation processing (left portion of chart).

Figure 6:
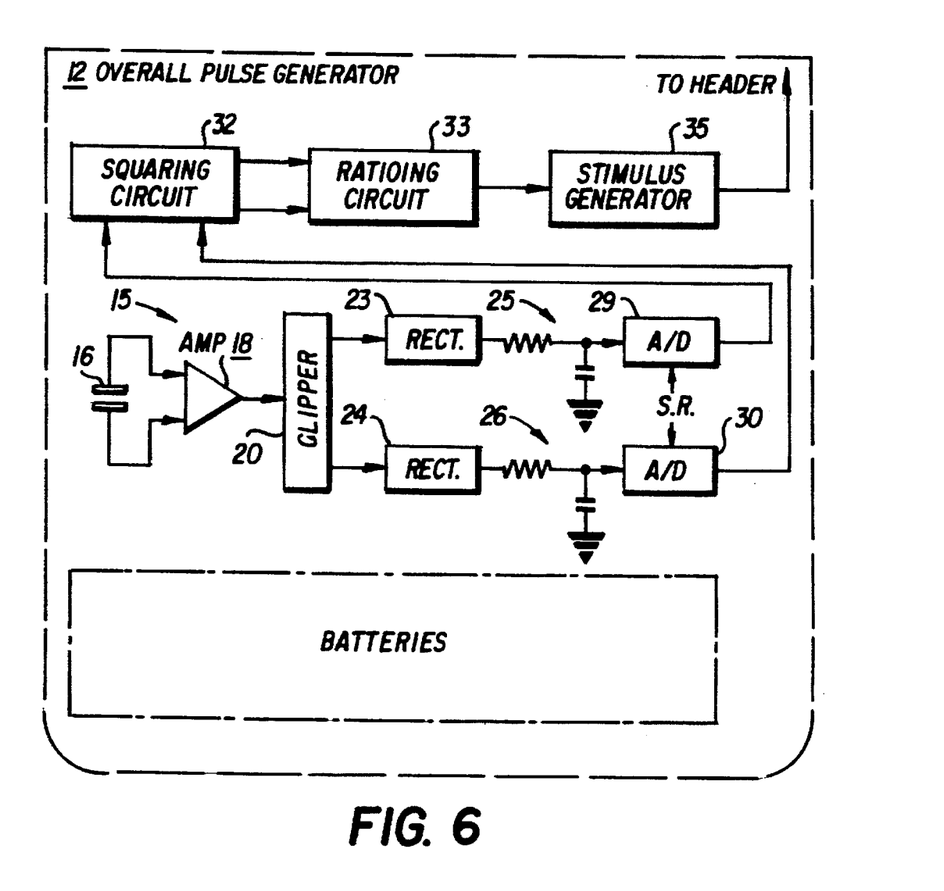
FIG. 6 is a simplified block diagram of an accelerometer-based, rate-adaptive pacer with signal processing and rate control components according to the present invention.

FIG. 6 is a simplified block diagram of a pacemaker pulse generator 12 featuring logic signal processing and rate control circuitry 15, employing leaky integrator and zero crossing detection, used for processing the signal derived from the accelerometer—here schematically represented by piezoelectric crystal 16. The output signal from the accelerometer is representative of patient movement/activity, as when the patient is walking. Details of a suitable accelerometer embodiment are contained in U.S. Pat. No. 5,031,615, the specification of which is incorporated herein by reference. The signal is amplified at 18, and positive and negative peaks are clipped at 20. The output is split into the positive and negative portions, which are subjected to full wave rectification at 23, 24. The individual rectifier outputs are applied to respective resistance-capacitance (RC) interval integrators and filters 25, 26 each with an RC time constant often seconds, for example. The signal is then subjected to analog-to-digital (A/D) conversion at 29, 30, and finally to squaring and ratioing (by division of the squared values) at 32, 33, for rate control of the pacing pulse rate by application to controllable variable pulse stimulus generator 35.

The A/D circuitry signal processing provide the final rate factor. Further aspects of relationship between accelerometer signal and final rate are described in U.S. Pat. Nos. 5,354,317 and 5,360,436, the specifications of which are incorporated herein by reference. The two integrators provide both positive and negative signal analysis relative to an electrical zero baseline for evaluation, tantamount to two leaky integrators. The processing indicates the portion of the signal that consists of positive components and the portion that consists of negative components relative to the electrical zero. Different types of zero crossings may be detected, one with respect to electrical zero and another with respect to a running average.

The interval integrator and filter has a specified time constant—here, 10 seconds, after which it returns to the baseline value. Zero crossings over electrical zero may be detected relative to a threshold so that less than the entire signal is considered, and may be analyzed from the standpoint of number of positive and negative zero crossings detected in a given time period. Then, the positive and negative portions or signal content are compared, and length of time positive vs. negative is compared. Alternatively, the integrated positive and negative areas of the signal may be compared. Rather than using an electrical zero baseline, a floating baseline may be used following low pass filtering. The raw signal is run through the low pass filter for averaging, and then the signal peaks above and below the average can be observed and compared.

The use of signal processing means such as signal squaring, or of multiplication factors, as discussed above, serves to emphasize the distinctions between the positive and negative signal portions, and thereby further discriminate the different types of walking activity of the patient to adapt the pacing rate to the type of activity. By these means, a clear distinction can be drawn between the patient walking on a level surface, walking up stairs, and walking down stairs, despite an apparent relatively uniform acceleration magnitude associated with those different types of activities.

A suitable formula that fits the final rate response according to the invention is the use of the integrated average amplitude of the acceleration signal over a time period—here, ten seconds, as the leaky integrator signal, or LIS, with addition of a second signal component consisting of LIS multiplied by a factor F times the quotient of the duration of the accelerometer signal in a positive direction above the zero baseline divided by the duration of the accelerometer signal in a negative direction below the zero baseline, expressed in a mathematical equation as follows:

$$\text{Heart pacing rate} = LIS + \{LIS \times f \times (\text{duration pos}/\text{duration neg})\}$$

Further signal processing means may be used to employ an addition of a cofactor to increase or decrease the quotient value, to square the positive quotient signal before it is divided by the negative component, and to use band-limiting factors for the zero crossing-derived quotient. In this way, a clear distinction can be derived between walking on a horizontal, walking up stairs, and walking down stairs.

The signal zero crossing when positive divided by the signal zero crossing when negative may be calculated as a ratio which discriminates between the patient walking upstairs and the patient walking downstairs. This can be achieved using a single leaky integrator. Calculation of area is not needed—the only matter of interest is the timing. That is, a determination is made of the time interval from the point in time at which a positive zero crossing occurred until the point in time at which a negative zero crossing occurs. Then, a division calculation is made to obtain a quotient of P/N. Preferably, the calculation is positive squared ($+^2$) divided by negative squared ($-^2$), to provide some amplification or enhancement of the result. The result is achieved by taking the peak level average, and then adding a function of amplitude times positive squared divided by negative squared.

An adjustment may be made for different results by setting the boundaries at different levels. F is a factor that amplifies the quotient, so the quotient may be taken fully or only partly. The highest rate is obtained with walking upstairs, the lowest rate with walking downstairs, and a median rate is achieved with walking on a level surface. An artificial limit may be introduced, such as where any signal above 2 is assumed to be 2, so this is cut off, and anything below 1 is assumed to be 1, after squaring. The leaky integrator peak average plus leaky integrator peak average times the ratio times the F factor. For example, the F factor may be 0.5—which provides the weighting of the raw signal and the correct signal—corresponding to a gain factor. The factor F may alternatively be arrived at empirically by performing simulations—to find the correct proportion between the raw signal and the modified signal—i.e., to modify the ratio.

Various embodiments of logic circuitry suitable for performing processing including calculations according to the principles of the invention are depicted within the logic circuitry of FIG. 6. For example, a signal content processor may be employed to weight the accelerometer sensor signal according to the signal content above and below the baseline level. Alternatively, the processor may calculate the ratio of the signal content above and below the baseline. In yet another embodiment, the signal content processor may compare areas occupied by the sensor signal portions lying above and below the baseline, and may include separate integrators for the positive and negative portions, together with a comparator. The same circuit may be characterized as capable of comparing an integral of the sensor signal portions above and below the baseline.

A further embodiment of a signal content processor may compare the amplitudes of the sensor signal portions above and below the baseline, such as by means of a pair of peak detectors followed by a comparator. Still another embodiment may be used for comparing successive time intervals during which the sensor signal portions remain above and below the baseline, using one or more interval detectors. Finally, the signal content processor may instead include circuitry for detecting successive zero crossings of the sensor signal relative to the baseline, and for calculating the ratio of time duration of the successive zero crossings in the positive and negative directions. In the latter case, the circuitry calculates the quotient of the respective positive and negative zero crossings as the ratio.

Thus, the invention provides implantable programmable rate responsive cardiac pacemakers which are capable of recognizing and responding differently to at least some of the multiple types of exercise in which the patient may engage. Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. A variable rate cardiac pacemaker adapted to be implanted in a human patient, for pacing the patient's heart at a rate according to metabolic need of the patient when walking on a grade, the pacemaker comprising:

sensor means responsive to patient walking to produce an electrical sensor signal representative of activity of the patient during the walking, said sensor signal having variable signal parameters indicative of morphology of the sensor signal, said parameters including amplitude of the sensor signal, said morphology being representative of current state of activity of the patient and inclination of a grade on which the patient is walking corresponding respectively to an ascending, descending, or level path;

control means responsive to said sensor signal for processing thereof to detect amplitude of said sensor signal and differences in the morphology of said sensor signal attributable to the respective grade on which the patient is walking, to produce a control signal therefrom dictating a pacing rate representative of amplitude of the sensor signal modified according to any said difference detected in the morphology of the sensor signal; said control means including content means for establishing a baseline level for the sensor signal and weighting the sensor signal according to signal morphology differences attributable to the patient walking on said respective grades by measuring predetermined characteristics of content of the sensor signal above and below said baseline level; and pulse generator means responsive to said control signal for generating pacing pulses at a variable rate according to patient activity, including differences in activity attributable to the patient walking on respective different grades, to be used for application to and electrical stimulation of the patient's heart.

2. The rate adaptive cardiac pacemaker of claim 1, in which:

said sensor means is an accelerometer.

3. The rate adaptive cardiac peacemaker of claim 1, in which:

said baseline level is electrical zero.

4. The rate adaptive cardiac pacemaker of claim 1, in which:

said content means includes means for measuring and calculating a ratio of said predetermined characteristics of signal content above and below said baseline level.

5. The rate adaptive cardiac pacemaker of claim 1, in which:

said characteristics of content comprise respective areas beneath a curve of sensor signal excursions above and below said baseline level, and said content means includes means for determining and comparing said respective areas above and below said predetermined baseline level as said morphology differences indicative of said differences in activity attributable to the patient walking on respective different grades.

6. The rate adaptive cardiac pacemaker of claim 1, in which:

said characteristics of content comprise respective integrals of a curve of said sensor signal lying above and below said baseline level, and said content means includes means for integrating and comparing said integrals of the sensor signal above and below said predetermined baseline level as said morphology differences indicative of said differences in activity attributable to the patient walking on respective different grades.

7. The rate adaptive cardiac pacemaker of claim 1, in which:

said characteristics of content comprise respective amplitudes of said sensor signal above and below said baseline level, and said content means includes means for detecting and comparing respective amplitude of the sensor signal above and below said predetermined baseline level as said morphology differences indicative of said differences in activity attributable to the patient walking on respective different grades.

8. The rate adaptive cardiac pacemaker of claim 1, in which:

said characteristics of content comprise respective time intervals of said sensor signal successively above and below said baseline level, and said content means includes means for detecting and comparing successive time intervals during which the sensor signal remains above and below said predetermined baseline level as said morphology differences indicative of said differences in activity attributable to the patient walking on respective different grades.

9. The rate adaptive cardiac pacemaker of claim 1, in which:

said characteristics of content comprise zero crossings of said sensor signal relative to said baseline level, and said content means includes means for detecting successive zero crossings of the sensor signal relative to said predetermined baseline level as said morphology differences indicative of said differences in activity attributable to the patient walking on respective different grades.

10. The rate adaptive cardiac pacemaker of claim 9, in which:

said content means further includes means for detecting and calculating a ratio of time duration of said successive zero crossings in a positive direction and in a negative direction relative to said predetermined baseline level.

11. The rate adaptive cardiac pacemaker of claim 10, in which:

said content means includes means for calculating a quotient of the detected respective positive and negative zero crossings as said ratio.

12. A device-implemented method for rate-responsive pacing of a human patient's heart to meet the metabolic needs of the patient when the patient is walking on a grade with an inclination constituting an ascending, descending, or level path, using a variable rate cardiac pacemaker adapted to be implanted in the patient, the method comprising the steps of:

sensing patient walking activity and responding thereto by producing an electrical sensor signal representative of such activity, said sensor signal having a pattern with variable parameters, including amplitude of the sensor signal, based on extent of patient activity including activity attributable to inclination of a grade on which the patient is walking;

generating pacing pulses at a controllably variable rate to electrically stimulate the patient's heart at a pacing rate based on patient activity; and processing said sensor signal to detect amplitude and pattern thereof and differences in the signal pattern attributable to extent of inclination of the respective grade on which the patient is walking, and controlling the rate of generation of the pacing pulses by establishing a basic pacing rate based on detected amplitude of the sensor signal, and deviating from said basic rate to provide a rate more appropriate to the metabolic needs of the patient based on detected differences in said signal pattern by establishing a baseline level and weighting the sensor signal according to a predetermined characteristic of content of said sensor signal above and below said baseline level as indicative of pacing rate variations required to accommodate activity level of the patient attributable to inclination of the grade on which the patient is walking.

13. The method of claim 12, in which:

said sensing of patient activity and responding thereto is performed by an accelerometer.

14. The method of claim 12, including:

establishing said baseline level as electrical zero.

15. A method of pacing the heart of a human patient using an implanted pacemaker device to automatically vary pacing rate according to whether the patient is engaged in types of activity characterized by walking up stairs, walking down stairs, or walking on a level surface, irrespective that intensity of the walking activity may be identical for all of said types of activity, comprising the device-implemented steps of:

sensing patient walking activity and producing an electrical sensor signal having an amplitude indicative of intensity thereof and a morphology that varies in at least one signal characteristic capable of distinguishing different ones among said types of the walking activity in which the patient is engaged;

establishing a baseline level of said sensor signal, and detecting variation of said at least one signal characteristic of the sensor signal morphology relative to said baseline level as indicating a specific one of said types of the patient's walking activity;

generating pacing pulses at a variable rate for use in electrically stimulating the patient's heart at a pacing rate that reflects metabolic need of the patient arising from walking activity; and providing a base pacing rate at which said pacing pulses are generated in response to the amplitude of said sensor signal and modifying the base pacing rate by weighting the sensor signal wording to the variation of said at least one signal characteristic of the sensor signal morphology above and below said baseline level to generate pacing pulses at a rate which is appropriate for said specific one of said types of walking activity in which the patient is engaged.

16. The method of claim 15, in which:

said step of sensing patient activity is performed by an accelerometer.

17. The method of claim 15, in which:

said baseline level is electrical zero.

\* \* \* \* \*